United States Patent
Strack et al.

(10) Patent No.: US 9,925,192 B2
(45) Date of Patent: Mar. 27, 2018

(54) METHOD FOR TREATING CANCER

(71) Applicant: Merck Sharp & Dohme Corp., Rahway, NJ (US)

(72) Inventors: Peter Strack, Reading, MA (US); Robert Booher, Davis, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/119,424

(22) PCT Filed: Feb. 23, 2015

(86) PCT No.: PCT/US2015/017008
§ 371 (c)(1),
(2) Date: Aug. 17, 2016

(87) PCT Pub. No.: WO2015/130585
PCT Pub. Date: Sep. 3, 2015

(65) Prior Publication Data
US 2017/0056406 A1    Mar. 2, 2017

Related U.S. Application Data

(60) Provisional application No. 61/946,139, filed on Feb. 28, 2014.

(51) Int. Cl.
| | | |
|---|---|---|
| A61K 31/497 | (2006.01) | |
| A61K 31/519 | (2006.01) | |
| A61K 45/06 | (2006.01) | |
| A61K 31/496 | (2006.01) | |
| A61K 9/00 | (2006.01) | |

(52) U.S. Cl.
CPC .......... *A61K 31/519* (2013.01); *A61K 9/0019* (2013.01); *A61K 9/0053* (2013.01); *A61K 31/496* (2013.01); *A61K 45/06* (2013.01)

(58) Field of Classification Search
CPC ............................ C07D 495/04; C07D 213/74

USPC ............................................ 514/253.1, 260.1
See application file for complete search history.

(56) References Cited

U.S. PATENT DOCUMENTS

| | | |
|---|---|---|
| 7,119,200 B2 | 10/2006 | Guzi et al. |
| 2014/0024610 A1 | 1/2014 | Pisani et al. |

FOREIGN PATENT DOCUMENTS

| | | |
|---|---|---|
| WO | 2011050016 A1 | 4/2011 |
| WO | 2012058392 A1 | 5/2012 |
| WO | 2013142281 A1 | 9/2013 |
| WO | 2013188355 A1 | 12/2013 |

OTHER PUBLICATIONS

Vandenberg et al., ABT-199, a new Bcl-2-specific BH3 mimetic, has in vivo efficacy against aggressive Myc-driven mouse lymphomas without provoking thrombocytopenia, Blood, Mar. 21, 2013, 2285-2288, 121:12.

Li et al., Targeting MCL1 and BCL2 in diffuse large B-cell lymphoma, J. Clin Oncol 32 (suppl; abstr e19509), 2014 [retrieved on Apr. 24, 2015], Retrieved from the internet. <URL: http://meetinglibrary.asco.org/content/126661-144>. see abstract.

Samantha M. Jaglowski et al. "Novel Therapies and Their Integration into Allogeneic Stem Cell Transplant for Chronic Lymphocytic Leukemia", Biology of Blood Marrow Transplantation, vol. 18, No. 1, pp. S132-S138, XP 02834705, ISSN: 1083-8791, DOI: 10.1016/J.BBMT.2011.11.018.

*Primary Examiner* — Raymond J Henley, III
(74) *Attorney, Agent, or Firm* — Catherine D. Fitch; Richard S. Parr

(57) ABSTRACT

A method for the treatment of cancer by administering a therapeutically effective amount of a cyclin-dependent kinase (CDK) inhibitor with a therapeutically effective amount of a B cell chronic lymphocytic leukemia/lymphoma 2 inhibitor ("B Cell CLL/Lymphoma 2", or "BCL-2"). Administration of the CDK inhibitor and BCL-2 inhibitor can be simultaneous, successive or separate.

20 Claims, 8 Drawing Sheets

METHOD FOR TREATING CANCER

BACKGROUND OF THE INVENTION

Pharmacologic approaches for treating cancer have traditionally relied on the use of various single agent systemic therapies (monotherapies). An archetypical example is chemotherapy, which utilizes broadly cytotoxic drugs that target rapidly dividing cells, or mitotic inhibitors to inhibit or kill the rapidly growing cells typical of cancer. Tumors may not be completely responsive to such monotherapy, either due to their high collateral systemic toxicity necessitating lower, even sub-therapeutic doses or development of tumor resistance that circumvents the activity of the monotherapy agent. More advanced chemotherapy strategies have been developed that are predicated on use of multiple agents in a combination therapy that simultaneously attack the tumor along multiple of biochemical pathways. Many of these regimens, such as the combination of doxorubicin, bleomycin, vinlastine and DTIC for Hodgkin's lymphoma, have been developed through empirical testing. Because of the inherent limitations of their individual pharmacologic components, such approaches remain relatively non-specific with high morbidity, allowing considerable room for improvement in terms of efficacy and safety.

Targeting cancers based on their selective overexpression of certain cell-surface receptors or reliance on specific signaling or metabolic pathways, in particular aberrant pathways present in certain cancers, provides another point of attack. For instance, it has been found that some cancers harbor mutations in certain protein kinases that are involved in cell signaling and hyperproliferative growth. Targeting these pathways through the use of inhibitors has proven attractive in controlling cancers by staving off oncolytic signaling. A similar approach based on targeting overexpression of certain receptors, such as epidermal growth factor receptor (EGFR) or vascular endothelial growth factor (VEGF), provides the basis for damping the oncolytic activity of these receptors, for instance by use of antibodies to the targeted receptors (or by use of agents that inhibit the signaling stimulated by these receptors). Unfortunately, as in the case of conventional chemotherapy, these receptors and pathways may play important physiologic roles peripheral to the tumor, leading to toxicity upon their targeting, while the targeted cells also may develop resistance by harnessing alternate biochemical processes or proliferating via selection of resistant clonal subpopulations of tumor cells. Thus, the challenges posed by these types of targeted therapies are substantially similar to those posed by conventional chemotherapy.

While the Cyclin-Dependent Kinase (CDK) inhibitor dinaciclib (((S)-(-)-2-(1-{3-ethyl-7-[(1-oxy-pyridin-3-ylmethyl)amino] pyrazolo[1,5-a]pyrimidin-5-yl} piperidin-2-yl)ethanol) has shown encouraging clinical effects in treating Chronic Lymphocytic Leukemia (CLL), its activity in other heme malignancies and solid tumors has been limited. Combination with the B Cell Chronic Lymphocytic Leukemia/Lymphoma 2 ("B Cell CLL/Lymphoma 2", or "BCL-2") inhibitor ABT-199 (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) has now been found to provide synergistic anti-tumor effects, and is well tolerated in preclinical tumor xenograft models.

SUMMARY OF THE INVENTION

The present invention is directed to a method for the treatment of cancer in a patient, said method comprising administering to the patient a therapeutically effective amount of a Cyclin-Dependent Kinase (CDK) inhibitor in combination with a therapeutically effective amount of a B Cell Chronic Lymphocytic Leukemia/Lymphoma 2 ("B Cell CLL/Lymphoma 2", or "BCL-2") inhibitor. Administration of the CDK inhibitor and BCL-2 inhibitor can be simultaneous, successive or separate.

DETAILED DESCRIPTION OF THE PRESENTLY PREFERRED EMBODIMENTS

Figure 1A:
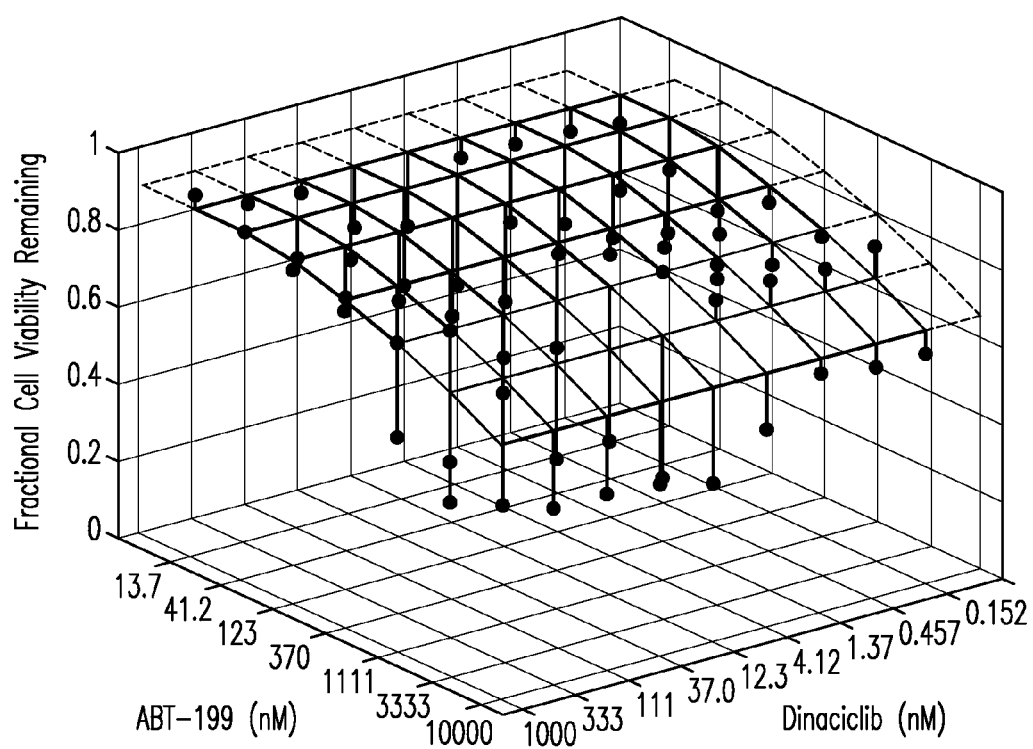
FIG. 1 Matrix dose response of dinaciclib and ABT-199 in vitro demonstrates synergy of combination (black dots) observed relative to added single agent response (wire mesh) in OVCAR8 (A) and RMUGS (B) ovarian cell lines, using Highest Single Agent (HSA) analysis.

In an embodiment of the method, the CDK inhibitor is dinaciclib (((S)-(-)-2-(1-{3-ethyl-7-[(1-oxy-pyridin-3-ylmethyl)amino] pyrazolo[1,5-a]pyrimidin-5-yl} piperidin-2-yl)ethanol) or pharmaceutically acceptable salt thereof, and the BCL-2 inhibitor is ABT-199 (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) or a pharmaceutically acceptable salt thereof. In an embodiment of this embodiment, the method involves intravenously administering dinaciclib and orally administering ABT-199. Administration of dinaciclib and ABT-199 can be simultaneous, successive or separate.

In an embodiment of the invention, the method involves intravenously administering about 6-28 mg/m$^2$ dinaciclib over a period of about 1-4 hours once every 5-9 days.

In an embodiment of the invention, the method involves intravenously administering about 12-14 mg/m$^2$ dinaciclib over a period of about 1-4 hours once every 5-9 days.

In an embodiment of the invention, the method involves intravenously administering about 12-14 mg/m$^2$ dinaciclib over a period of about 2 hours once every 5-9 days.

In an embodiment of the invention, the method involves intravenously administering about 12-14 mg/m$^2$ dinaciclib over a period of about 2 hours once every 7 days.

In an embodiment of the invention, the method involves intravenously administering about 30-70 mg/m$^2$ dinaciclib over a period of about 1-4 hours once every 18-24 days.

In an embodiment of the invention, the method involves intravenously administering about 50 mg/m² dinaciclib over a period of about 1-4 hours once every 18-24 days.

In an embodiment of the invention, the method involves intravenously administering about 50 mg/m² dinaciclib over a period of about 2 hours once every 18-24 days.

In an embodiment of the invention, the method involves intravenously administering about 50 mg/m² dinaciclib over a period of about 2 hours once every 21 days.

In an embodiment of the invention, the method involves daily orally administering ABT-199.

In an embodiment of the invention, the method involves daily orally administering about 20-900 mg ABT-199.

In an embodiment of the invention, the method involves daily orally administering about 20-400 mg ABT-199.

In an embodiment of the invention, the method involves daily orally administering about 50-400 mg ABT-199.

In an embodiment of the invention, the method involves daily orally administering about 50 mg ABT-199.

In another embodiment of the method, the cancer is a heme malignancy or solid tumor. In an embodiment of this embodiment, the heme malignancy is leukemia or lymphoma, and the solid tumor is a sarcoma, carcinoma or lymphoma.

The present invention is also directed to a pharmaceutical composition for the treatment of cancer comprising: a therapeutically effective amount of a CDK inhibitor; and a therapeutically effective amount of a BCL-2 inhibitor. In an embodiment of the composition, the CDK inhibitor is dinaciclib (((S)-(−)-2-(1-{3-ethyl-7-[(1-oxy-pyridin-3-ylmethyl)amino] pyrazolo[1,5-a]pyrimidin-5-yl} piperidin-2-yl)ethanol) or a pharmaceutically acceptable salt thereof, and the BCL-2 inhibitor is ABT-199 (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) or a pharmaceutically acceptable salt thereof.

The present invention is also directed to a combination comprising a cyclin-dependent kinase inhibitor and a B cell chronic lymphocytic leukemia/lymphoma 2 inhibitor for use in the treatment of cancer. The present invention is also directed to this combination wherein the cyclin-dependent kinase inhibitor is dinaciclib and the B cell chronic lymphocytic leukemia/lymphoma 2 inhibitor is ABT-199. The present invention is also directed to the use of a combination comprising a cyclin-dependent kinase inhibitor and a B cell chronic lymphocytic leukemia/lymphoma 2 inhibitor, for the manufacture of a medicament for the treatment of cancer. The present invention is also directed to the use of a combination comprising dinaciclib and ABT-199 for the manufacture of a medicament for the treatment of cancer. These combinations can be administered simultaneously, separately or sequentially Dinaciclib is described in U.S. Pat. No. 7,119,200. Unless otherwise indicated, references below to dinaciclib also include pharmaceutically acceptable salts thereof. For preparing dinaciclib pharmaceutical compositions, inert, pharmaceutically acceptable carriers can be either solid or liquid. Solid form preparations include powders, tablets, dispersible granules, capsules, cachets and suppositories. The powders and tablets may be comprised of from about 5 to about 95 percent dinaciclib. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa. Liquid form preparations of dinaciclib include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Aerosol preparations of dinaciclib suitable for inhalation may include solutions and solids in powder form, which may be in combination with a pharmaceutically acceptable carrier, such as an inert compressed gas, e.g. nitrogen. Also included are solid form preparations of dinaciclib that are intended to be converted, shortly before use, to liquid form preparations of dinaciclib for either oral or parenteral administration. Such liquid forms include solutions, suspensions and emulsions. Dinaciclib may also be deliverable transdermally. The transdermal compositions can take the form of creams, lotions, aerosols and/or emulsions and can be included in a transdermal patch of the matrix or reservoir type as are conventional in the art for this purpose. Dinaciclib may also be delivered subcutaneously. The pharmaceutical preparation can be in unit dosage form. In such form, the preparation is subdivided into suitably sized unit doses containing appropriate quantities of dinaciclib, e.g., an effective amount to achieve the desired purpose. The quantity of dinaciclib in a unit dose of preparation may be varied or adjusted from about 1 mg to about 100 mg, more specifically from about 1 mg to about 50 mg, more specifically from about 1 mg to about 25 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

ABT-199 is described in PCT International Publication WO201150016 and PCT International Publication WO2012058392. Unless otherwise indicated, references below to ABT-199 also include pharmaceutically acceptable salts thereof.

The term "pharmaceutically acceptable salt" as referred to in this description means ordinary, pharmaceutically acceptable salt. For example, when the compound has a hydroxyl group, or an acidic group such as a carboxyl group and a tetrazolyl group, then it may form a base-addition salt at the hydroxyl group or the acidic group; or when the compound has an amino group or a basic heterocyclic group, then it may form an acid-addition salt at the amino group or the basic heterocyclic group. The base-addition salts include, for example, alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts. The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The term "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic. These solid preparations such as tablets, capsules, granules and powders may generally contain, for example, 0.1 to 100% by weight, and specifically 5 to 98% by weight, based on the total weight of each preparation. Liquid preparations are produced in the forms of suspension, syrup, injection and drip infusion (intravenous fluid) using appropriate additives that are conventionally used in liquid preparations, such as water, alcohol, or a plant-derived oil, such as, soybean oil, peanut oil, and sesame oil. In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof. Such injection may be in a form of a preliminarily dissolved solution, or in a form of powder per se or powder associated with a suitable carrier (additive) that is dissolved at the time of use. The injection liquid may contain, for example, 0.1 to 10% by weight of an active ingredient based on the total weight of each preparation. Liquid preparations such as suspension or syrup for oral administration may contain, for example, 0.1 to 10% by weight of an active ingredient based on the total weight of each preparation.

Each preparation used in the invention can be prepared by a person having ordinary skill in the art according to conventional methods or common techniques. For example, a preparation can be carried out, if the preparation is an oral preparation, for example, by mixing an appropriate amount of dinaciclib or ABT-199 with an appropriate amount of lactose and filling this mixture into hard gelatin capsules which are suitable for oral administration. On the other hand, preparation can be carried out, if the preparation containing dinaciclib or ABT-199 is an injection, for example, by mixing an appropriate amount of dinaciclib or ABT-199 with an appropriate amount of 0.9% physiological saline and filling this mixture in vials for injection.

As used herein, the term "composition" is intended to encompass a product comprising the specified ingredients in the specified amounts, as well as any product that results, directly or indirectly, from combination of the specified ingredients in the specified amounts.

Dosing and Routes of Administration

With regard to dinaciclib and ABT-199, various solid and liquid preparation forms can be selected, and examples thereof include oral preparations such as tablets, capsules, powders, granules or liquids, or sterilized liquid parenteral preparations such as solutions or suspensions, suppositories, ointments and the like. Dinaciclib and ABT-199 are available as pharmaceutically acceptable salts. Dinaciclib and ABT-199 are prepared with pharmaceutically acceptable carriers or diluents.

The amount and frequency of administration of dinaciclib and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, more specifically 1 mg/day to 200 mg/day, in two to four divided doses. More specifically, dinaciclib can be intravenously administered in amounts of about 6-28 mg/m$^2$, and more specifically about 12-14 mg/m$^2$, over a period of about 1-4 hours, more specifically about 2 hours, about every 5-9 days, more specifically about every 7 days. Alternatively, dinaciclib can be intravenously administered in amounts of about 30-70 mg/m$^2$, more specifically about 50 mg/m$^2$ over a period of about 1-4 hours, more specifically about 2 hours, about every 18-24 days, more specifically about every 21 days.

Doses of ABT-199 specifically range from 0.1 mg/kg to 100 mg/kg, daily or twice a week, administered, for example, in 0.1 ml i.p. for 3 weeks. A more typical recommended daily dosage regimen for oral administration can range from about 20-900 mg, more specifically 20-400 mg, more specifically 50-400 mg, and more specifically about 50 mg.

Dinaciclib and ABT-199 can be prepared for simultaneous, separate, or successive administration.

Dinaciclib and ABT-199 may be administered to mammals, including humans, either together or, additionally with, pharmaceutically acceptable carriers, excipients or diluents, in a pharmaceutical composition, according to standard pharmaceutical practice. The components can be administered orally or parenterally, including the intravenous, intramuscular, intraperitoneal, subcutaneous, rectal and topical routes of administration.

Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

The term "administration" and variants thereof (e.g., "administering" a compound) in reference to a component of the invention means introducing the component or a prodrug of the component into the system of the animal in need of treatment. When a component of the invention or prodrug thereof is provided in combination with one or more other active agents, "administration" and its variants are each understood to include concurrent and sequential introduction of the component or prodrug thereof and other agents.

The term "therapeutically effective amount" as used herein means that amount of active compound or pharmaceutical agent that elicits a biological or a medicinal response in a tissue, system, animal or human that is being sought by a researcher, veterinarian, medical doctor or other clinician. This includes combination therapy involving the use of multiple therapeutic agents, such as a combined amount of a first and second treatment where the combined amount will achieve the desired biological or medicinal response. The desired biological response can be partial or total inhibition, delay or prevention of the progression of cancer, including cancer metastasis; inhibition, delay or prevention of the recurrence of cancer, including cancer metastasis; or the prevention of the onset or development of cancer (chemoprevention) in a mammal, for example a human.

The term "simultaneous" as referred to in this description means that the pharmaceutical preparations of the invention are administered simultaneously in time.

The term "separate" as referred to in this description means that the pharmaceutical preparations of the invention are administered at different times during the course of a common treatment schedule.

The term "successive" as referred to in this description means that administration of one pharmaceutical preparation is followed by administration of the other pharmaceutical preparation; after administration of one pharmaceutical preparation, the second pharmaceutical preparation can be administered substantially immediately after the first pharmaceutical preparation, or the second pharmaceutical preparation can be administered after an effective time period after the first pharmaceutical preparation; and the effective time period is the amount of time given for realization of maximum benefit from the administration of the first pharmaceutical preparation.

The term "patient" as referred to in this description includes a mammal, e.g., human, afflicted with a cancer condition. The patient may be a human in need of treatment to alleviate the condition, and may also be a human receiving treatment for the cancer condition.

The term "cancer" as referred to in this description includes various sarcoma and carcinoma and includes solid cancer and hematopoietic cancer. The solid cancer as referred to herein includes, for example, brain cancer, cervicocerebral cancer, esophageal cancer, thyroid cancer, small cell lung cancer, non-small cell lung cancer, breast cancer, endometrial cancer, lung cancer, stomach cancer, gallbladder/bile duct cancer, liver cancer, pancreatic cancer, colon cancer, rectal cancer, ovarian cancer, choriocarcinoma, uterus body cancer, uterocervical cancer, renal pelvis/ureter cancer, bladder cancer, prostate cancer, penis cancer, testicles cancer, fetal cancer, Wilms' tumor, skin cancer, malignant melanoma, neuroblastoma, osteosarcoma, Ewing's tumor, soft part sarcoma. On the other hand, the hematopoietic cancer includes, for example, acute leukemia, chronic lymphatic leukemia, chronic myelocytic leukemia, polycythemia vera, malignant lymphoma, multiple myeloma, Hodgkin's lymphoma, non-Hodgkin's lymphoma.

The term "treatment of cancer" as referred to in this description means that an anticancer agent is administered to a cancer case so as to inhibit the growth of the cancer cells in the case. Specifically, the treatment results in cancer growth regression, or that is, it reduces the size of a detectable cancer. More specifically, the treatment results in complete disappearance of cancer.

Additional Indications

In addition to, and also specifically with regard to the treatment of heme malignancy and solid tumors, the method is useful for treating breast cancer, melanoma, colorectal cancer, non-small cell lung cancer and ovarian cancer, and the following other cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

Reference to the specific embodiments set forth above is meant to include all combinations of particular and specific groups unless stated otherwise. In the Example detailed below, approximate tumor sizes and body weight are measured twice a week. Average volumes and standard deviations are calculated for each group and plotted. References to dinaciclib in these examples mean (((S)-(−)-2-(1-{3-ethyl-7-[(1-oxy-pyridin-3-ylmethyl)amino] pyrazolo[1,5-a]pyrimidin-5-yl} piperidin-2-yl)ethanol). References to ABT-199 in these examples mean (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}, sulfonyl)-2-(1H-pyrrolo[2,3-b]pyridin-5-yloxy) benzamide).

Example 1

In Vitro Methods

Cell lines were purchased from ATCC, DSMZ, or under an agreement, and cultured in provider recommended media with 10% fetal bovine serum (FBS, Invitrogen) at 37° C. and 5% $CO_2$. Exception was that all Diffuse Large B-cell Leukemia (DLBCL) cells were cultured in media containing Heat-inactivated Fetal Bovine Serum (HI-FBS, Sigma), supplemented with 10 mM HEPES (Thermo) and 1× Non-Essential Amino Acids (Gibco). All cell lines were grown in exponential growth phase. Small Cell Lung Cancer (SCLC) or DLBCL cells were cultured at a density of $0.5-2.5 \times 10e^6$ cells/ml. All cell lines were seeded at 20,000 cells/well in 100 µl to 96 well plates before compound addition of dinaciclib (0.1 µM), ABT-199 (1.0 µM), or the dinaciclib plus ABT-199 (combination). Following 8 hours of compound treatment cell viability was measured using Cell Titer Glo (Promega).

Matrix dose combinations: Adherent cells cultured in exponential growth phase were trypsinized, counted using a Vi-Cell (Beckman Coulter), seeded at 1000 cells per well into 384 well solid white ScreenMates plates (Matrix), and allowed to culture overnight. The following day, 3-fold serial dilutions of dinaciclib and ABT-199 in DMSO were combined to generate a full 10×8 dose response matrix, and then added to cells in quadruplicates such that the final DMSO concentration was 0.5%. After 24 hours, proliferation was measured using Cell Titer Glo (Promega) on a Synergy (BioTek) reader and converted to fractional values based on internal plate controls. Compound synergy was determined using the Highest Single Agent (HSA) method. Excess volumes, integrated over the full dose response matrix, greater than 0.1 were considered synergistic.

In Vivo Models:

NCI-H82 Human Small Cell Lung Xenograft:

Eight week old female athymic nude mice (Crl:NU(NCr)-Foxn1nu) with body weights ranging from ~18.0 to 25 grams were used for this study. NCI-H82 tumor cells were grown to mid-log phase in RPMI-1640 medium containing 10% fetal bovine serum, 100 units/mL penicillin G, 100 µg/mL streptomycin sulfate, 25 µg/mL gentamicin and 2 mM glutamine. The cells were cultured in tissue culture flasks in a humidified incubator at 37° C., in an atmosphere of 5% $CO_2$ and 95% air. Mice were implanted subcutaneously in the right flank with $5 \times 10e^6$ NCI-H82 tumor cells in 50% matrigel in a total volume of 0.2 ml. Eight days after inoculation, mice were randomized into groups when tumors reached an average tumor volume of ~150 $mm^3$.

Toledo Human Diffuse Large B-Cell Lymphoma (DLBCL) Xenograft:

Eight week old female SCID beige mice (Fox Chase SCID® Beige) with body weights ranging from 18.0 to 22 grams were used for this study. Toledo tumor cells were grown to mid-log phase in RPMI-1640 medium containing 10% fetal bovine serum, 100 units/mL penicillin G, 100 µg/mL streptomycin sulfate, and 10 mM sodium pyruvate. The cells were cultured in tissue culture flasks in a humidified incubator at 37° C., in an atmosphere of 5% $CO_2$ and 95% air. Mice were implanted subcutaneously in the right flank with $5 \times 10e^6$ tumor cells in 50% matrigel in a total volume of 0.1 ml. Twenty-eight days after inoculation, mice were randomized into groups when tumors reached an average tumor volume of ~160 $mm^3$.

SUDHL4 Human Diffuse Large B-Cell Lymphoma (DLBCL) Xenograft:

Eight week old female SCID Beige mice with body weights ranging from ~17.0 to 25 grams were used for this study. SU-DHL-4 tumor cells were grown to mid-log phase in RPMI-1640 medium containing 10% fetal bovine serum, 100 units/mL penicillin G, 100 µg/mL streptomycin sulfate, 25 µg/mL gentamicin and 2 mM glutamine. The cells were cultured in tissue culture flasks in a humidified incubator at 37° C., in an atmosphere of 5% $CO_2$ and 95% air. Mice were implanted subcutaneously in the right flank with $10 \times 10e6$ SU-DHL-4 (DSMZ) tumor cells in 50% matrigel in a total volume of 0.2 ml. Twenty two days after inoculation, mice were randomized into groups when tumors reached an average tumor volume of ~135 mm3. Dosing was only conducted for eleven days (3 cycle of dinaciclib, 11 cycles of ABT-199). Following that treatment period tumor regrowth was monitored.

Dosing/Administration:

Dinaciclib, formulated in 20% hydroxypropyl beta-cyclodextrin (HPBCD), was dosed at 40 mg/kg intraperitoneal (ip) every four days (q4d). ABT-199 formulated in 10% ethanol, 30% polyethylene glycol (PEG) 400 and 60% Phosal 50 PG was dosed at 100 mg/kg orally (po), daily (qd)×28. Both test agents were administered at 10 ml/kg.

Statistical Analysis:

Tumor volume (TV) was measured twice a week using calipers. Tumor volume was calculated by the elliptical formula: Tumor Volume=width2×length/2. Body weight was measured at least twice weekly. Anti-tumor activity is reported as tumor growth inhibition (% TGI) where: % TGI=[−100×(mean TV treated end−mean TV treated start)/(mean TV control end−mean TV control start)]+100. Statistical Analysis of Tumor Growth Inhibition (TGI) was analyzed by one-way ANOVA followed by Tukey's multiple comparison test.

Results:

The in vitro anti-cancer activity of dinaciclib (0.1 uM) and ABT-199 (1 uM) was tested alone and in combination against cell lines of Small Cell Lung Cancer (SCLC) and Diffuse Large B-cell Lymphoma (DLBCL) following 8 hours of treatment. The combination of these two agents resulted in a 7.0-64.9% decrease in cell viability compared to the best single agent activity (Table 1). These data demonstrate the rapidity (<8 hours) within which anti-cancer combination benefit can be obtained with this combination.

Figure 1B:
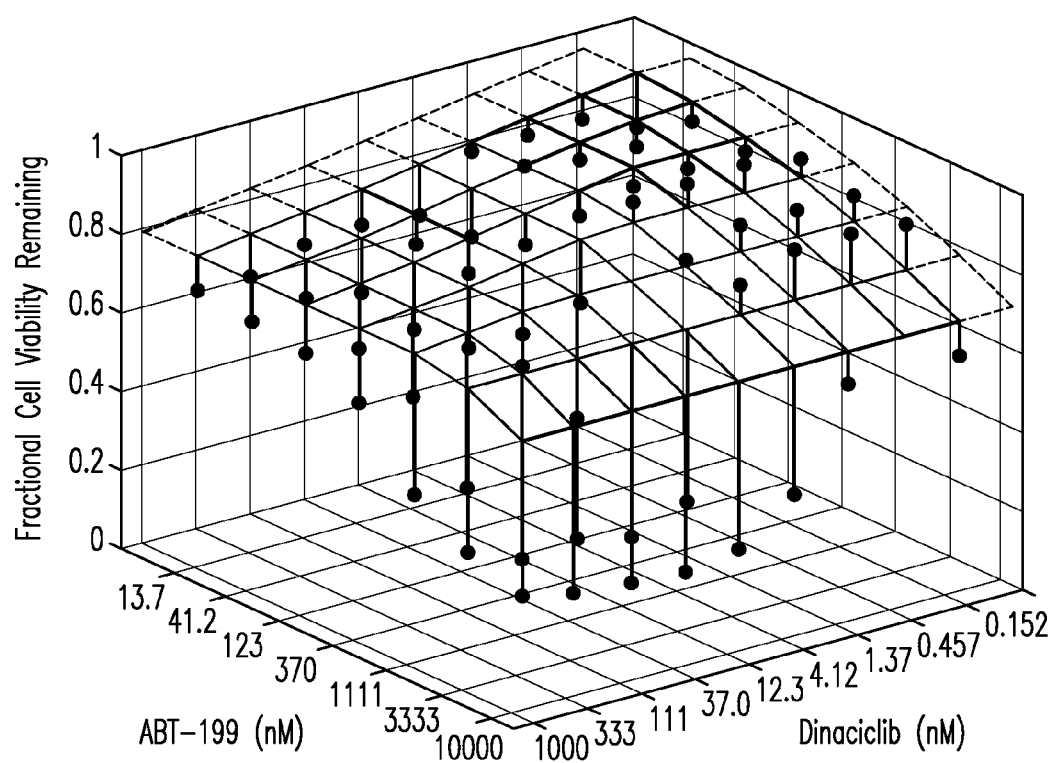

To determine whether the combination the benefit observed was synergistic, a 9 point dose response of dinaciclib and ABT-199 was tested in an overlapping matrix format using ovarian cell lines. Synergy of the combination was observed as excess volume (FIG. 1, black dots) relative to the highest single agent response of either single agent alone (FIG. 1, wire mesh plot) in two ovarian cell lines, OVCAR8 (FIG. 1 (A)) and RMUGS (FIG. 1 (B)), as well as, the Diffuse Large B-cell lines HBL1, TOLEDO, U2932.

The excess volume observed was also reported as the Highest Single Agent (HSA) value using methods described by Lehar, J. et al., Chemical combination effects predict connectivity in biological systems. *Molecular Systems Biol-* ogy 2007, 3:1-14. The score of >0.1 (p<0.001) demonstrated the anti-cancer synergy obtained by combining dinaciclib with ABT-199 (Table 2).

To determine whether the synergy observed in vitro provided anti-tumor benefit in vivo, we evaluated the combination at doses reported to be effective as single agents in preclinical xenograft models (Parry, D., et al., Dinaciclib (SCH 727965), a Novel and Potent Cyclin-Dependent Kinase Inhibitor. Mol. Can. Therap. 2010, 9:2344-2353; Souers, A. J., et al. ABT-199, a potent and selective BCL-2 inhibitor, achieves antitumor activity while sparing platelets. Nat. Med. 2013, 19:202-208.).

Figure 2A:
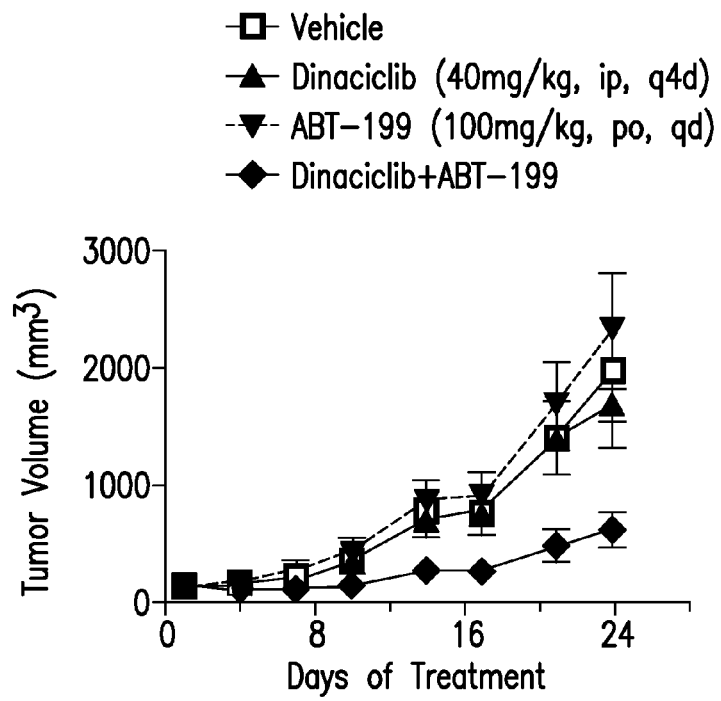
FIG. 2 Antitumor effects in the NCI-H82 Small Cell Lung Cancer (SCLC) mouse xenograft model: (A) tumor volume versus days of treatment; (B) tumor volume resulting from treatment with vehicle, dinaciclib, ABT-199 or combination of dinaciclib+ABT-199; and (C) tumor body weight change versus days of treatment.
Figure 2B:
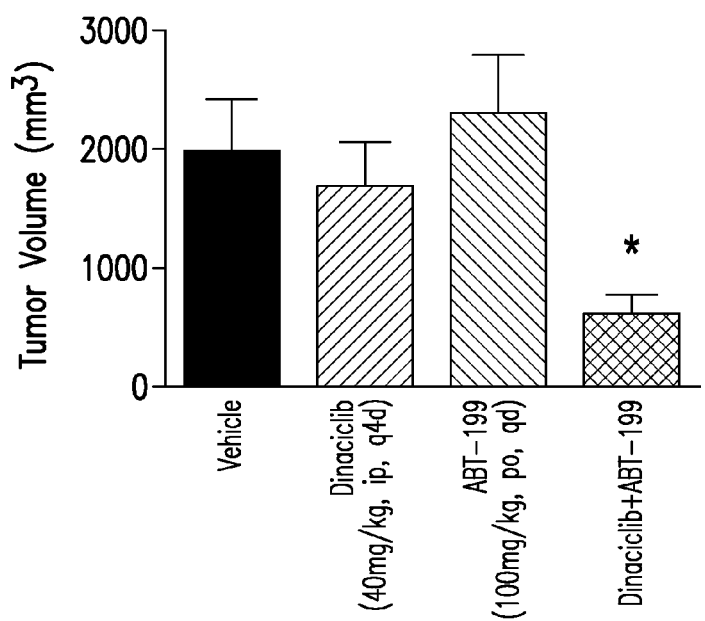
Figure 2C:
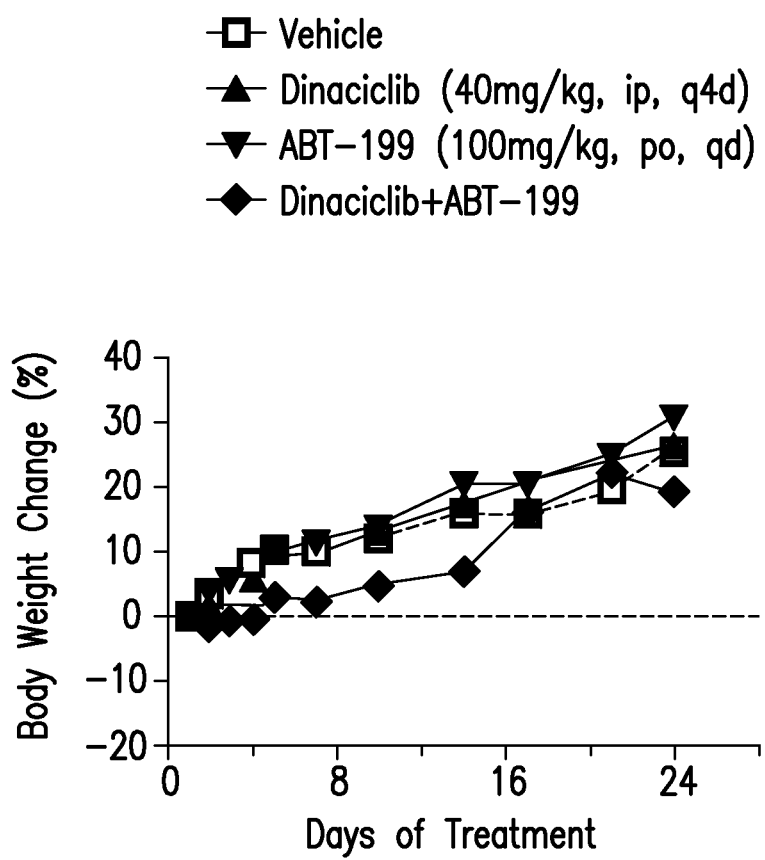

Dinaciclib and ABT-199 as single agents had no effect on tumor growth in the NCI-H82 human Small Cell Lung Cancer (SCLC) xenograft model at these doses (FIG. 2A). In contrast however, the combination of dinaciclib and ABT-199 provided anti-tumor benefit, resulting in 79% (* p<0.05) Tumor Growth Inhibition (TGI) at end of study (FIGS. 2A & 2B). This combination was well tolerated at single dose levels as measured by NCI-H82 xenograft body weight (FIG. 2C). These data demonstrate that the combination of dinaciclib with ABT-199 can provide unrealized anti-cancer benefit in situations where neither agent is active alone.

Figure 3A:
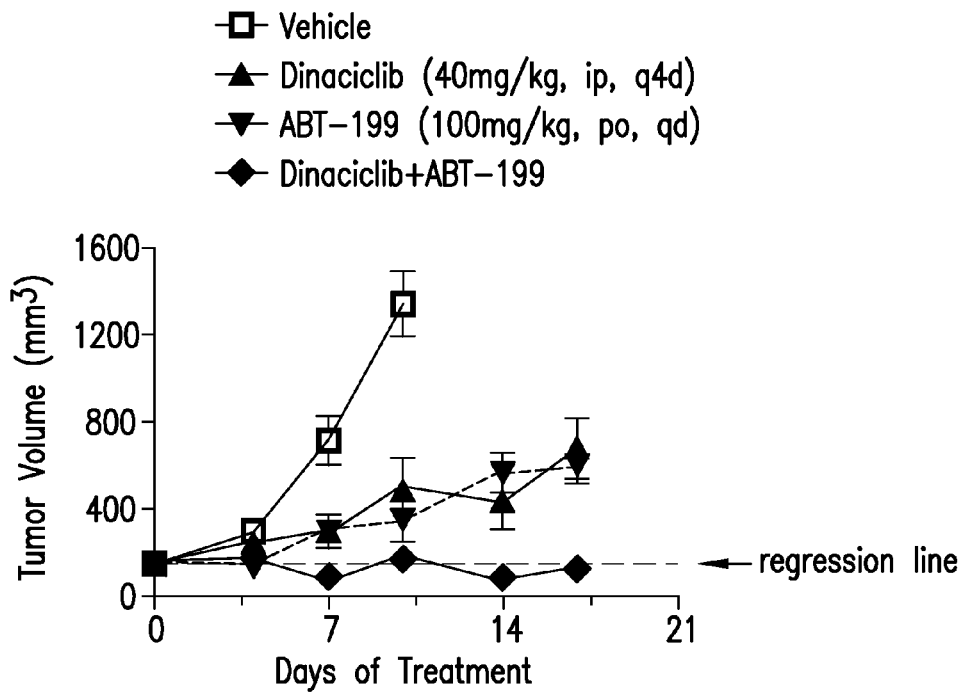
FIG. 3 Antitumor effects in the Toledo Diffuse Large B-Cell Leukemia (DLBCL) mouse xenograft model: (A) tumor volume versus days of treatment; (B) tumor volume resulting from treatment with vehicle, dinaciclib, ABT-199 or combination of dinaciclib+ABT-199; and (C) tumor body weight change versus days of treatment.
Figure 3B:
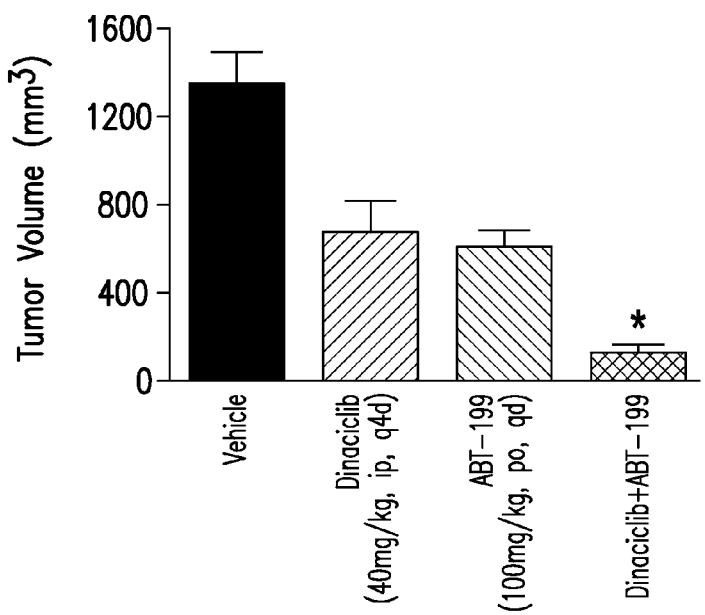
Figure 3C:
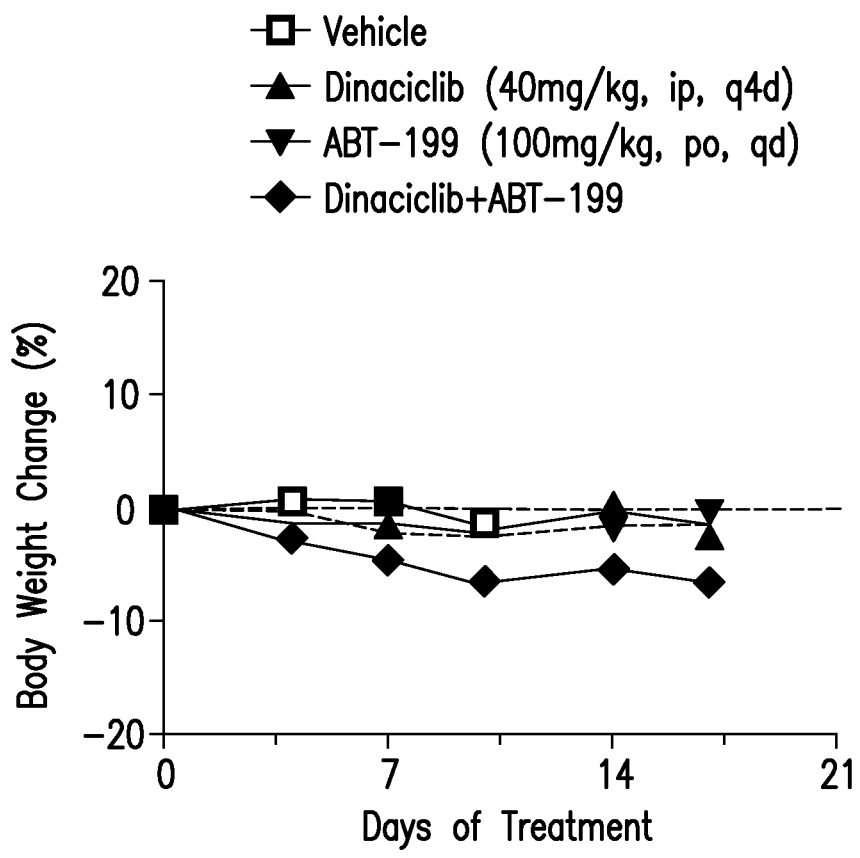

In the TOLEDO human Diffuse Large B-Cell Lymphoma (DLBCL) xenograft model, dinaciclib and ABT-199 alone provided anti-tumor effects, however, the combination of dinaciclib with ABT-199 resulted in anti-tumor benefit that was greater than either dinaciclib or ABT-199 alone and to a degree which resulted in tumor regression (FIGS. 3A & 3B). The combination was also well tolerated in this model as measured by xenograft body weight (FIG. 3C).

Figure 4A:
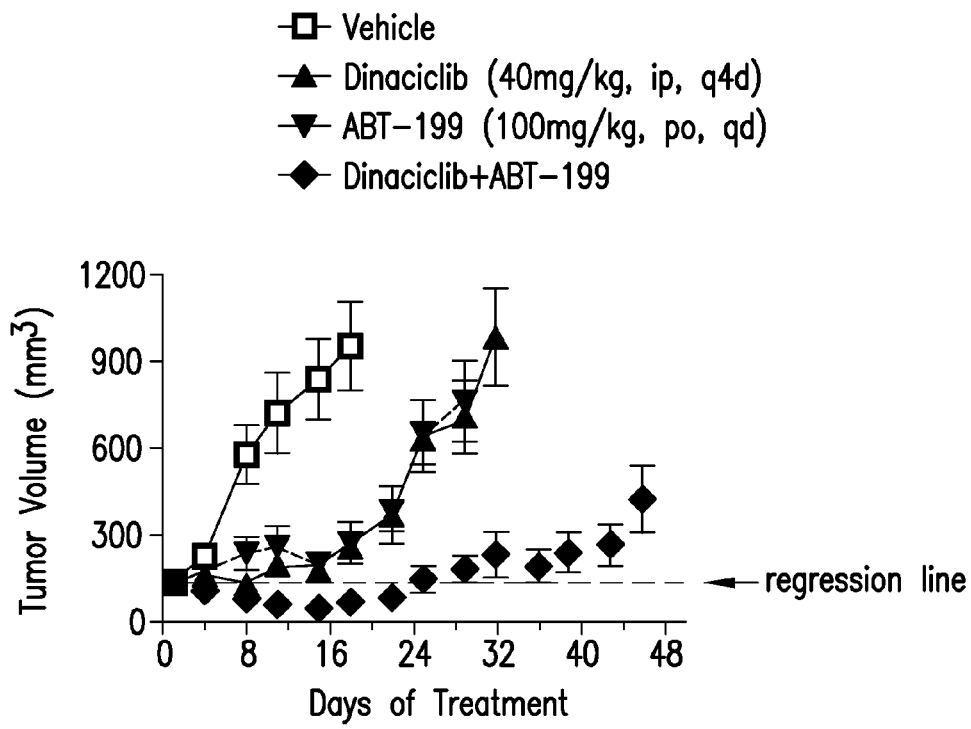
FIG. 4 Antitumor effects in the SUDHL4 Diffuse Large B-Cell Leukemia (DLBCL) mouse xenograft model: (A) tumor volume versus days of treatment; (B) tumor volume resulting from treatment with vehicle, dinaciclib, ABT-199 or combination of dinaciclib+ABT-199; and (C) tumor body weight change versus days of treatment.
Figure 4B:
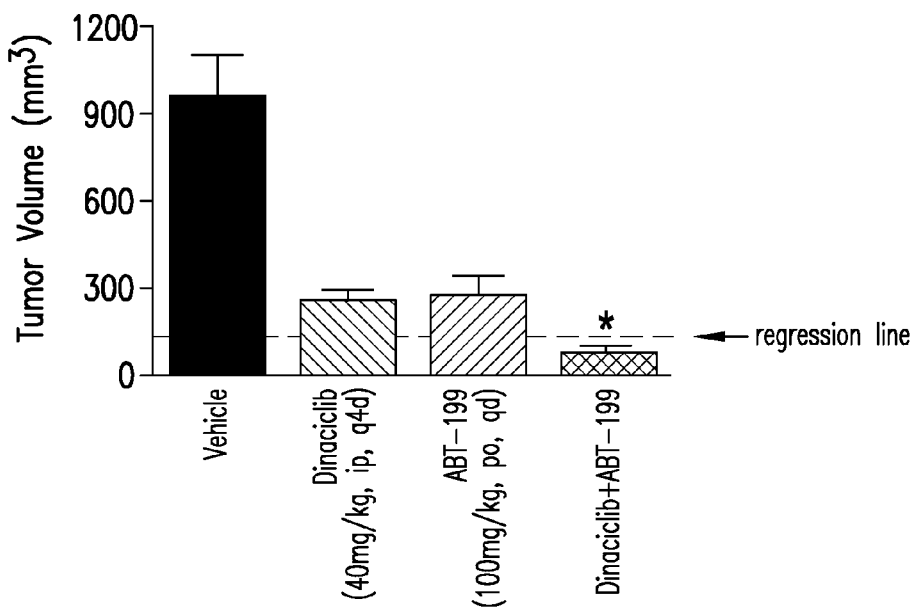
Figure 4C:
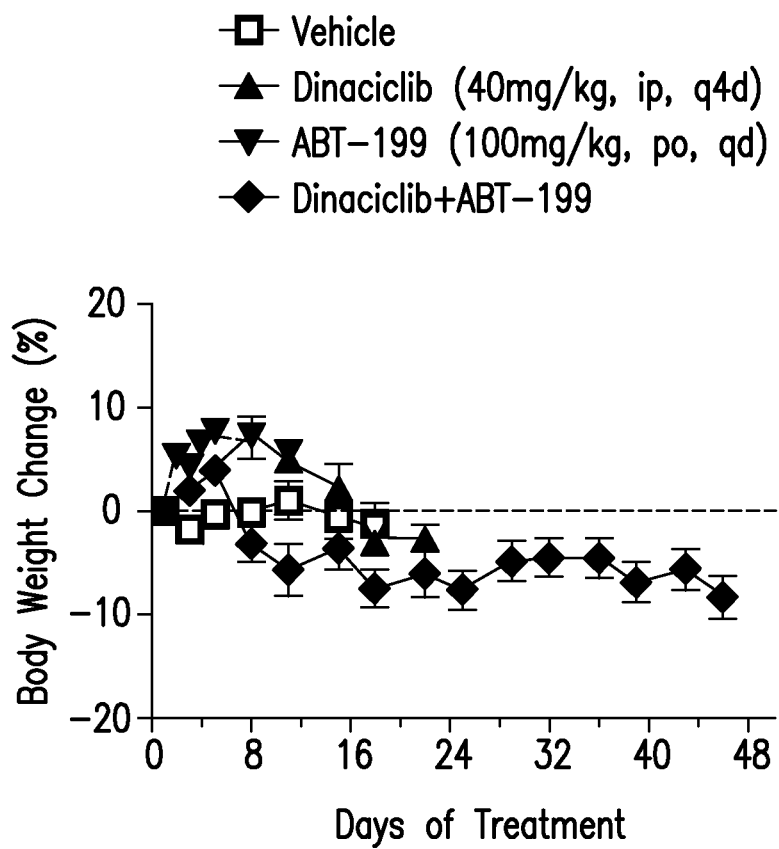

In a second DLBCL xenograft model SUDHL4, single agent activity of dinaciclib and ABT-199 was observed, demonstrating the doses used in this and previous studies have the ability to induce anti-tumor effect in cases where it was not observed. Similar to the other models described, the combination of dinaciclib with ABT-199 provided combination benefit that was greater (*p<0.05) than either single agent alone as measured on day 18 (FIGS. 4A & 4B). These data also provide evidence of a second model where the combination of dinaciclib and ABT-199 was capable of inducing tumor regression (8%, day 18) (FIG. 4A). The increase in tumor volume observed at later time points with the combination was associated with the termination of treatment on day 11, but still provided delayed tumor growth to day 48, at which time the study was ended (FIG. 4A). In this model the combination was again well tolerated as measured by SUDHL4 xenograft body weight, at dose levels where each single agent had shown anti-tumor activity (FIG. 4C).

These data demonstrate that the combination of the CDK inhibitor dinaciclib with the BCL2 inhibitor ABT-199 can rapidly decrease cancer cell viability and provide unrealized combination benefit to tumor regression in models where the single agents showed no or partial activity. Importantly, the combination of these agents is well tolerated at single dose levels utilized.

This description has been offered for illustrative purposes only and is not intended to limit the invention of this application.

TABLE 1

Combination of dinaciclib and ABT-199 shows anti-cancer benefit with 8 hours of treatment in vitro.

| | | % Viability Remaining (8 hr) | | | | | | |
|---|---|---|---|---|---|---|---|---|
| | | ABT-199 (1 uM) | | Dinaciclib (0.1 uM) | | Combination | | Combination |
| cell name | cancer type | mean | sd | mean | sd | mean | sd | benefit |
| H82 | SCLC | 110.6 | 7.6 | 64.7 | 8.1 | 57.7 | 1.3 | 7.0 |
| H146 | SCLC | 92.6 | 4.1 | 117.8 | 3.1 | 78.0 | 0.8 | 14.5 |
| H128 | SCLC | 95.4 | 10.7 | 114.1 | 3.2 | 30.5 | 0.9 | 64.9 |
| Su-DHL-4 | DLBCL | 85.4 | 2.0 | 53.5 | 0.8 | 12.9 | 0.4 | 40.5 |
| Su-DHL-8 | DLBCL | 99.4 | 0.5 | 125.9 | 2.8 | 71.1 | 4.0 | 28.2 |

TABLE 2

Combination of dinaciclib and ABT-199 provides synergistic anti-cancer benefit in vitro as measured by Highest Single Agent (HSA) score

| Cell Line | Excess Volume (HSA) | p value |
|---|---|---|
| OVCAR8 | 0.16 | <0.001 |
| RMUGS | 0.13 | <0.001 |
| HBL1 | 0.12 | <0.001 |
| TOLEDO | 0.15 | <0.001 |
| U2932 | 0.17 | <0.001 |

What is claimed is:

1. A method for the treatment of cancer, said method comprising administration of a therapeutically effective amount of a cyclin-dependent kinase inhibitor in combination with a therapeutically effective amount of a B cell chronic lymphocytic leukemia/lymphoma 2 inhibitor, wherein the cancer is diffuse large B-cell leukemia or small cell lung cancer.

2. A method of claim 1, wherein the cyclin-dependent kinase inhibitor is dinaciclib or pharmaceutically acceptable salt thereof, and the B cell chronic lymphocytic leukemia/lymphoma 2 inhibitor is ABT-199 or a pharmaceutically acceptable salt thereof.

3. A method of claim 2, comprising intravenously administering dinaciclib and orally administering ABT-199.

4. A method of claim 3, comprising intravenously administering about 6-28 mg/m$^2$ dinaciclib over a period of about 1-4 hours once every 5-9 days.

5. A method of claim 4, comprising intravenously administering about 12-14 mg/m$^2$ dinaciclib over a period of about 1-4 hours once every 5-9 days.

6. A method of claim 5, comprising intravenously administering about 12-14 mg/m$^2$ dinaciclib over a period of about 2 hours once every 5-9 days.

7. A method of claim 6, comprising intravenously administering about 12-14 mg/m$^2$ dinaciclib over a period of about 2 hours once every 7 days.

8. A method of claim 3, comprising intravenously administering about 30-70 mg/m$^2$ dinaciclib over a period of about 1-4 hours once every 18-24 days.

9. A method of claim 8, comprising intravenously administering about 50 mg/m$^2$ dinaciclib over a period of about 1-4 hours once every 18-24 days.

10. A method of claim 9, comprising intravenously administering about 50 mg/m$^2$ dinaciclib over a period of about 2 hours once every 18-24 days.

11. A method of claim 10, comprising intravenously administering about 50 mg/m² dinaciclib over a period of about 2 hours once every 21 days.

12. A method of claim 3, comprising daily orally administering ABT-199.

13. A method of claim 12, comprising daily orally administering about 20-900 mg ABT-199.

14. A method of claim 13, comprising daily orally administering about 20-400 mg ABT-199.

15. A method of claim 14, comprising daily orally administering about 50-400 mg ABT-199.

16. A method of claim 15, comprising daily orally administering about 50 mg ABT-199.

17. A pharmaceutical composition comprising a therapeutically effective amount of a cyclin-dependent kinase inhibitor; and a therapeutically effective amount of a B cell chronic lymphocytic leukemia/lymphoma 2 inhibitor.

18. A pharmaceutical composition of claim 17, wherein the cyclin-dependent kinase inhibitor is dinaciclib or pharmaceutically acceptable salt thereof, and the B cell chronic lymphocytic leukemia/lymphoma 2 inhibitor is ABT-199 or a pharmaceutically acceptable salt thereof.

19. A combination comprising a cyclin-dependent kinase inhibitor and a B cell chronic lymphocytic leukemia/lymphoma 2 inhibitor for use in the treatment of cancer, wherein the cancer is diffuse large B-cell leukemia or small cell lung cancer.

20. The combination of claim 19 wherein the cyclin-dependent kinase inhibitor is dinaciclib and the B cell chronic lymphocytic leukemia/lymphoma 2 inhibitor is ABT-199.

* * * * *